(12) United States Patent
Zühlke et al.

(10) Patent No.: US 8,632,795 B2
(45) Date of Patent: Jan. 21, 2014

(54) DEVICE FOR DISPENSING BARK BEETLE PHEROMONE IN A CONTROLLED MANNER

(75) Inventors: Thomas Zühlke, Rödersheim-Gronau (DE); Jürgen Jentzsch, Gerwisch (DE); Ulf Baier, Ichtershausen (DE); Hansjochen Schroeter, Kirchzarten (DE)

(73) Assignee: BASF SE, Ludwigshafen (DE)

( * ) Notice: Subject to any disclaimer, the term of this patent is extended or adjusted under 35 U.S.C. 154(b) by 1663 days.

(21) Appl. No.: 11/791,943

(22) PCT Filed: Nov. 30, 2005

(86) PCT No.: PCT/EP2005/012786
§ 371 (c)(1),
(2), (4) Date: May 30, 2007

(87) PCT Pub. No.: WO2006/058729
PCT Pub. Date: Jun. 8, 2006

(65) Prior Publication Data
US 2008/0014171 A1    Jan. 17, 2008

(30) Foreign Application Priority Data
Dec. 1, 2004  (DE) .......................... 10 2004 058 052

(51) Int. Cl.
*A01N 25/34*  (2006.01)
(52) U.S. Cl.
USPC ................. 424/409; 43/108; 43/131; 424/84; 424/405; 514/462; 514/549; 514/739
(58) Field of Classification Search
None
See application file for complete search history.

(56) References Cited
U.S. PATENT DOCUMENTS 5,223,542 A * 6/1993 Byers et al. ................... 514/691
5,750,129 A * 5/1998 Wakarchuk ................... 424/408

FOREIGN PATENT DOCUMENTS

DE    9002948        7/1990
EP    024396.3       10/1987
EP    0273197        7/1988
EP    0413325        2/1991

OTHER PUBLICATIONS

Abstract Biosis: 1989:180430 of Journal of Applied Entomology (1989) vol. 107,# 1 pp. 1-31 Comparative Studies on Semiochemicals in Pityogenes—SPP.*
Baader, Von E.J., "*Pityogenes* spp. (Col., Scolytidae): Untersuchungen über verhaltenssteuernde Duftstoffe und deren Anwendung im Waldschutz[1]", J. Appl. Ent., 1989, pp. 1-31, vol. 107, Search Report.
Dubbel, V., et al., "Optimierung der Falleneinsatzes bei Buchdrucker und Kupferstecher", Forsttechnische Informationen, 1996, pp. 77-80, vol. 8/96, Search Report.
Vaupel, O., "Möglichkeiten der Verminderung von Borkenkäferschäden durch die Anwendung von Pheromonfallen", 1990, pp. 80-93, vol. 267, Search Report.

* cited by examiner

*Primary Examiner* — Neil Levy
(74) *Attorney, Agent, or Firm* — Brinks Gilson & Lione

(57) ABSTRACT

The present invention relates to a device in the form of a container made of a polymer material, which container has one or more sealed chambers, each of which comprise a liquid pheromone comprising 2-ethyl-1,6-dioxaspiro[4,4]nonane, methyl 2,4-decadiene-carboxylate and at least one alcohol selected among 2-methylbut-3-en-2-ol and 2-methylbut-3-yn-2-ol, where at least 50% of the area of the walls forming the chambers have a wall thickness in the range of from 0.1 to 1 mm and the polymer material which forms the chamber is at least in those areas an uncoated vinyl acetate/ethylene copolymer with a vinyl acetate content in the range of from 10 to 17% by weight. The invention also relates to a method of combating and for monitoring the swarming behavior of the species *Pityogenes chalcographus*, generally also referred to as spruce wood engraver or six-dentated bark beetle.

11 Claims, 1 Drawing Sheet

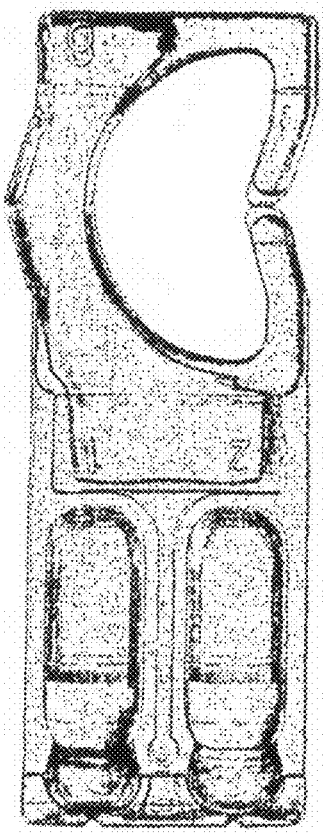

DEVICE FOR DISPENSING BARK BEETLE PHEROMONE IN A CONTROLLED MANNER

The present invention relates to a device for the controlled release of the pheromone of the six-dentated bark beetle. The invention also relates to a method for combating and for controlling the swarming behavior of the species *Pityogenes chalcographus*, generally also referred to as spruce wood engraver or six-dentated bark beetle.

Pheromones have become increasingly important as means for controlling insects in the protection of forests. A large number of pheromones which act as lures for pests in forests, for example bark beetles, are known. A review can be found for example in J. Vitae, Biologie in unserer Zeit 8, 112 (1978). A widely used method for employing pheromones in the control of pests is mass trapping in trap systems, with the pheromones acting as lures. This requires suitable active ingredient dispensers which ensure a sustained uniform release of the active ingredients and thus lead to successful trapping.

The six-dentated bark beetle is one of the most feared pests, in particular in spruce stands. In contrast to other bark beetle species, the six-dentated bark beetle not only damages the trunk regions, where any attack of the trees is evident from entry holes and boring dust, but also the crown, which is difficult to control. Moreover, it also occurs in pole wood, which is difficult to control, in plantations, and in the crowns of old trees, a fact which is largely unknown in other beetle species as far as spruces are concerned. Because of these peculiarities, the findings obtained in the control of other beetles are with regularity impossible to apply to the six-dentated bark beetle.

Monitoring the swarming behavior and trapping the six-dentated bark beetle, which are important measures for reducing outbreaks in standing timber, i.e. the attack on trees which appear healthy, is done using technical traps and/or trap trees or trap wood piles which are equipped with a nature-identical aggregation lure combination (pheromone). A pheromone which is suitable as lure combination for the six-dentated bark beetle is a mixture of 2-ethyl-1,6-dioxaspiro[4,4]nonane with methyl 2,4-decadienecarboxylate and 2-methylbut-3-yn-1-ol or 2-methylbut-3-en-1-ol (herein below also referred to as pheromone of the six-dentated bark beetle). For a high degree of attraction, all components of this mixture must be present in sufficient amounts since the six-dentated bark beetle reacts with great sensitivity to the absence of even one of these components, which is a problem in terms of trap performance.

Usually, the pheromones are released via a dispenser in the form of a polyethylene film bag in which there is arranged a cellulosic absorbent material which is impregnated with the pheromone (which consists of at least three active ingredients). Such dispensers are available from BASF Aktiengesellschaft under the trade name Chalcoprax® DISP. The pheromone is released through the polyethylene film by diffusion.

The disadvantage of these dispensers is that, depending on the weather conditions, pheromone release is largely uncontrolled. The pheromone concentration in the saturated material, which is high initially, drops more and more rapidly as time passes; the point in time when the release of the lure has ended cannot be specified. This is why frequently the termination of the trap devices' performance for trapping the six-dentated bark beetle is erroneously equated with the end of swarming. Frequently, however, the actual cause for a decline in the trapping performance is exhaustion of the active ingredient or insufficient release of the pheromone by the dispenser, whatever the reason. This is why the user has to rely on his experience alone to determine the point in time at which the conventional dispenser must be exchanged before the release of the lure may have ended. Possible application errors or other factors (for example climatic factors) which prematurely lead to poor release of the lure, or none at all, are difficult to identify. Likewise, dispensers which are still operative are replaced merely as a precaution to ensure that as many six-dentated bark beetles as possible are destroyed. To prevent these uncertainties regarding the release of active ingredients, at least two, occasionally even three, traditional dispensers are necessarily required during the flying season, which is unnecessary expense for the user.

There is therefore a need for dispensers which are suitable for providing controlled release of the lure combination for the six-dentated bark beetle over a prolonged period.

EP-A 243 263 discloses a hollow-chamber dispenser for pheromone-based insect lures, which dispenser is made of a polyolefin or a copolymer of olefin and vinyl acetate with a vinyl acetate content of less than 20% by weight. For regulating the permeation of lures, these dispensers are equipped with an impermeable or sparingly permeable coating. The lures mentioned are 14-methyloctadec-1-ene and E-5-decenyl acetate. Such dispensers have proved to be unsuitable for the controlled release of the pheromone of the six-dentated bark beetle.

EP 413 325 A2 describes a device for combating the eight-dentated bark beetle which comprises one or two closed chambers which are filled with the pheromone of the eight-dentated bark beetle (mixture of ipsdienol, verbenol and methylbutenol), the wall material of which chambers being an ethylene/vinyl acetate copolymer which has a vinyl acetate content of 10 to 15% by weight and which is coloured with an inorganic pigment. Such devices are likewise unsuitable for combating the six-dentated bark beetle.

The object of the invention is therefore to provide a device which permits reliable control of the swarming of the six-dentated bark beetle and the reliable combating of the latter, even under adverse climatic conditions such as a change in temperature and light conditions or high temperatures even over a prolonged period. In particular, the method should also permit effective control of this pest in an environment which is difficult to control, for example in areas with wind-thrown trees (beetle gap) and/or in old stands since current methods are unsatisfactory here.

Surprisingly, it has now been found that this object can be achieved by a device in the form of a container made of a plastic material, which container has one or more sealed chambers, each of which comprise a liquid pheromone comprising 2-ethyl-1,6-dioxa-spiro[4,4]nonane, methyl 2,4-decadienecarboxylate and at least one alcohol selected among 2-methylbut-3-en-2-ol and 2-methylbut-3-yn-2-ol, where at least 50% of the area of the walls forming the chambers have a wall thickness in the range of from 0.1 to 1 mm and the plastic material which forms the chamber is at least in those areas an uncoated vinyl acetate/ethylene copolymer with a vinyl acetate content in the range of from 10 to 17% by weight.

Accordingly, the present invention relates to such a device. As a result of the release characteristics of the active ingredient, this device is particularly suitable for combating and monitoring beetles of the species *Pityogenes chalcographus*. Subject matter of the present invention is therefore also the use of such devices in combating and monitoring the six-dentated bark beetle, and a method for combating the six-dentated bark beetle where one or more devices according to the invention are employed together in conjunction with trapping devices.

An essential aspect of the present invention is the nature of the wall material of the chambers since the walls which surround the chambers constitute the barrier through which the lure combination diffuses and is then released into the environment in a controlled manner. It is assumed that this specific wall material absorbs the pheromone like a sponge and then releases it in a controlled manner so that this specific wall material acts like a buffer which compensates for variations in the release rate brought about by the weather. In accordance with the invention, at least 50%, preferably at least 70%, in particular at least 90% and in particular all of the wall area which surrounds the chambers of the device are formed by the ethylene/vinyl acetate copolymer. The latter preferably has a vinyl acetate content in the range of from 12 to 15% by weight, and at least the wall area zones being uncoated. A uniform release of the active ingredient constituents of the active ingredient solution comprised in the chambers is no longer ensured outside these delimitations.

In a first preferred embodiment, the wall material is essentially uncolored. This means that the vinyl acetate/ethylene copolymer which forms the walls of the chamber comprises less than 1% by weight and in particular less than 0.5% by weight and especially preferably no color-imparting constituents such as inorganic or organic pigment or other dyes. Devices in which the walls of the chambers are formed by an essentially uncolored vinyl acetate/ethylene copolymer ensure to a particularly high degree that reliable trap performance is maintained under extreme weather conditions, in particular during prolonged hot spells.

In another embodiment, the wall material of the chambers is formed by a colored vinyl acetate/ethylene copolymer which comprises up to 50% by weight, usually of from 1 to 30% by weight, of colorant, for example pigment, in particular red and/or brown pigments.

The vinyl acetate/ethylene copolymer which is employed as the wall material may comprise small amounts of stabilizers, for example antioxidants, which are conventionally used for such polymers and which prevent or reduce aging of the plastic material. Such stabilizers can be present in the polymer in amounts of up to 0.1% by weight. In addition, the polymer may also comprise conventional amounts of processing auxiliaries such as antiblocking agents and lubricants, for example erucamide or oleamide. These do not have adverse effects on the properties of the device.

Furthermore, it has proved advantageous for the vinyl acetate/ethylene copolymer to have a melt flow index in the range of from 1.8 to 3.2 g/10 min and in particular in the range of from 2.2 to 2.8 g/10 min, determined by ASTM D 1238 at 190° C. and a load of 2.16 kg.

Such vinyl acetate/ethylene copolymers are known from the prior art and commercially available, for example under the trade names Greenflex ML, in particular Greenflex® ML 40 from Polimeri SA, Italy.

Besides the vinyl acetate/ethylene copolymer, which accounts for at least the major part of the chamber wall, the devices according to the invention may also comprise further materials, for example materials for mechanically connecting a plurality of chambers or for stabilizing the device against mechanical damage or for attaching the device to trees or in traps. Preferably, however, the device according to the invention is made exclusively of the vinyl acetate/ethylene copolymer.

The device according to the invention comprises the liquid pheromone of the six-dentated bark beetle in the chambers. As a rule, the total amount of lure combination amounts to 2 to 10 ml per device and in particular 1 to 5 ml and specifically 1.5 to 2.5 ml per chamber. Preferred is a lure combination which comprises 2-ethyl-1,6-dioxaspiro[4,4]nonane in a concentration of from 2 to 10% by weight and in particular from 4 to 8% by weight based on the total weight of the lure combination. The concentration of the decadienyl ester in the lure combination is preferably in the range of from 0.5 to 5% by weight, in particular in the range from 1 to 2% by weight. The amount of 2-methylbut-3-yn-2-ol is as a rule at least 50% by weight and is in particular in the range from 80 to 97% by weight. In particular, the lure combination comprises no further constituents, apart from small amounts of impurities which are due to the manufacturing process, and any stabilizers which may be present.

As opposed to the film bag of the prior art, the devices according to the invention are shaped, i.e. three-dimensional, articles having at least 2, for example 2, 3 or 4, chambers for accommodating the pheromone of the six-dentated bark beetle. To ensure uniform release of the pheromone, at least 50%, in particular at least 70% of the wall areas which form the chambers have a wall thickness in the range of from preferably 0.2 to 0.6 mm and in particular in the range of from 0.25 to 0.5 mm. According to the invention, at least these areas are formed by the ethylene/vinyl acetate copolymer and are uncoated.

The geometry of the chambers can be spherical, ellipsoid, polyhedral, cylindrical or irregularly shaped. Preferably, most of the chamber has a tubular geometry, it being possible for the cross-sectional area of the tube to be circular, star-shaped, rectangular, elliptical, polygonal or irregularly shaped. Frequently, the cross-section has a circular or ellipsoidal geometry or a rectangular geometry with rounded edges. The internal volume of each of the chambers is usually in the range of from 1 to 5 $cm^3$.

Furthermore, it has proved advantageous for the ratio of the area of the walls forming the chamber in question to the internal volume of the chamber in question to be in the range of from 1 to 10 $cm^{-1}$ and in particular in the range of from 2 to 6 $cm^{-1}$. Preferably, tubular chambers have an internal diameter in the range from 5 to 20 mm, or a cross-sectional area in the range of from 20 to 200 $mm^2$ and a length in the range of from 15 to 40 mm. The ends of these tubular chambers can be sealed as desired, for example by concave or planar surfaces.

In a preferred embodiment, the device according to the invention has two chambers. If the device according to the invention has two or more chambers, they are separate from one another, i.e. they have no connections which fluids may pass through.

Besides the chamber(s), the device according to the invention may also be equipped with means for attaching the device in baited traps, for example recesses for passing through fixing means such as wire and the like.

An example of a device according to the invention which is made of uncolored vinyl acetate/ethylene copolymers and which is filled with pheromone as shown in FIG. 1.

The devices according to the invention can be manufactured in analogy to prior-art vials which are filled with active ingredients, for example by blow molding, double stretch-forming or in particular by thermoforming, where, as a rule, the chambers are filled in the same pass.

The devices according to the invention have a series of advantages:

In contrast to the traditional dispensers, the devices according to the invention ensure a continuous release of the pheromone in an effective amount. Also, variations in the concentration of the pheromone constituents which are released do not occur in contrast to the conventional dispensers, or not to an extent which would adversely affect the trapping performance. In contrast to the conventional film bag dispensers, which have to be changed empirically after 8 to 10 weeks, the device according to the invention ensures the release of the pheromone quantity and composition required for accurate trapping performance after a matter of 14 weeks. Moreover, the device according to the invention enables for the first time the reliable deduction of the end of swarming from the fact that the trap equipped with the device according to the invention stands empty. Moreover, the devices according to the invention also ensure reliable monitoring of swarming at problem locations such as old stands.

A further advantage is the improved controllability of the hollow-chamber dispenser. Since the wall material chosen and the wall thickness mean that the device is transparent, the fill level can always be read accurately so that the point in time at which the device has to be replaced can be determined precisely. While—independently of any residual pheromone which may still be present—the conventional dispenser was disposed of after swarming had ended because of the lack of reliable trapping performance, this device according to the invention can be checked accurately for residual amounts, if appropriate stored carefully for the next year under cool conditions and then reused.

Thus, the invention dramatically improves the reliability during monitoring and the performance of trapping the six-dentated bark beetle and thus reliably permits the reduction of outbreaks in standing timber. Moreover, the simple fabrication, checking of remaining residual amounts and reusability after storage contribute not only to cost savings, but also to reduced amounts of refuse.

The devices according to the invention can thus be employed in the customary way for combating beetles of the species Pityogenes chalcographus. As a rule, they will be employed together with beetle traps, with trap wood piles, trap trees, trap brushwood piles or trap poles which are optionally treated with a suitable insecticide, for example α-cypermethrin. Methods for this purpose are known to the skilled worker, for example from Forsttechnische Informationen, 1996 (8), pp. 77-80 and from the manufacturer's product details on Chalcoprax®, for example from the product information of BASF Aktiengesellschaft.

The devices according to the invention will frequently be combined with trapping devices such as slit traps from Theysohn, which may be arranged for example as three-trap stars or as individual traps. The joint use of the trapping device combined with the device according to the invention together with other trapping devices such as trap wood piles, trap poles, trap brushwood piles or trap trees is also suitable for combating the six-dentated bark beetle.

The devices according to the invention can also be used for monitoring purposes. To this end, they will generally be placed in individual traps, for example at endangered locations of spruce thickets, pole woods, but also older stands.

To reduce outbreaks in standing timber, one or more devices according to the invention will be employed together with traps or trap wood piles, trap poles, trap brushwood piles or trap stacks which are treated with a suitable insecticide, for example α-cypermethrin, at locations where outbreaks have already taken place in standing or lying timbers after the timber which has suffered the outbreak has been cleared away.

The examples which follow are intended to illustrate the invention, but without imposing any limitations.

EXAMPLE 1

Device with two chambers as shown in FIG. 1, which consists of an uncolored vinyl acetate/ethylene copolymer with the following properties:

vinyl acetate content: 14% by weight;

melt flow index: 2.50 g/10' (at 190° C./2.16 kg as specified in ASTM-D 1238)

flexural modulus: 60 mPa (ASTM D790)

The length of the chambers is in each case approx. 30 mm, the mean diameter approx. 1.2 mm, the volume per chamber when empty is approximately 2.8 ml. The wall thickness of the chambers in the half facing the attachment is 391±30 µm.

The chambers were filled with in total 2000 mg (fill weight) of a mixture of 6-7% by weight of 2-ethyl-1,6-dioxaspiro[4,4]nonane, 1-2% by weight of methyl 2,4-decadiene-carboxylate and 91-93% by weight of 2-methylbut-3-yn-2-ol.

EXAMPLE 2

Device with two chambers as described in FIG. 1, the wall material consisting of a vinyl acetate/ethylene copolymer which is colored brown and has the following properties:

vinyl acetate content: 14% by weight;

melt flow index: 2.50 g/10' (at 190° C./2.16 kg as specified in ASTM-D 1238)

flexural modulus: 60 mPa (ASTM D790)

COMPARATIVE EXAMPLE 1

Device with two chambers as described in Example 1, the wall material consisting of an LD polyethylene colored brown (LUPOLEN 3020 D, BASELL).

COMPARATIVE EXAMPLE 2

Device with two chambers as described in Example 1, the wall material consisting of an LD polyethylene colored white with titanium dioxide (LUPOLEN 2920 K, BASELL).

COMPARATIVE EXAMPLE 3

Device with two chambers as described in Example 1, the wall material consisting of a polyethylene colored white with titanium dioxide (LUPOLEN 1840 H, BASELL).

COMPARATIVE EXAMPLE 4

Device with two chambers as described in Example 1, the wall material consisting of a polyethylene uncolored with titanium dioxide (LUPOLEN 2420 H, BASELL).

COMPARATIVE EXAMPLE 5

Commercially available film bag dispenser Chalcoprax® Disp from BASF Aktiengesellschaft, filled with 1.8 g of the pheromone of Example 1.

Study of the Evaporation Behavior:

The devices filled with pheromone were tested for weight loss every 8 to 18 days over a period of approximately 3.5 months (Apr. 30, 2003 to Aug. 10, 2003) under field conditions. To this end, the devices were hung inside slit traps from Theysohn. The location was Gerwisch/Magdeburg. The traps were in the shade in the morning and in the sun from mid-day. The results in Table 1 are the means for in each case 10 devices.

TABLE 1

| Example | | \multicolumn{11}{c}{Date} | | | | | | | | | | |
|---|---|---|---|---|---|---|---|---|---|---|---|---|
| | | 30.4 | 10.5. | 18.5. | 5.6. | 14.6. | 25.6. | 3.7. | 10.7. | 19.7. | 27.7. | 3.8. | 10.8. |
| 1 | [mg][1] | 0 | 253 | 619 | 782 | 916 | 1095 | 1238 | 1449 | 1596 | 1703 | 1730 | 1733 |
| | [%][2] | 100 | 87.3 | 69.1 | 60.9 | 54.2 | 45.3 | 38.1 | 27.6 | 20.2 | 14.9 | 13.5 | 13.4 |
| 2 | [mg][1] | 0 | 376 | 396 | 703 | 933 | 1138 | 1277 | 1390 | 1486 | 1610 | 1754 | 1822 |
| | [%][2] | 100 | 81.2 | 80.2 | 64.9 | 53.3 | 43.1 | 36.1 | 30.5 | 25.7 | 19.5 | 12.3 | 8.9 |
| C1 | [mg][1] | 0 | 68 | 71 | 220 | 220 | 226 | 229 | \multicolumn{6}{l}{Experiment cancelled} |
| | [%][2] | 100 | 96.6 | 96.5 | 89.0 | 89.0 | 88.7 | 88.6 | | | | | |
| C2 | [mg][1] | 0 | 40 | 78 | 153 | 176 | 226 | 301 | \multicolumn{6}{l}{Experiment cancelled} |
| | [%][2] | 100 | 98 | 96.1 | 92.4 | 91.2 | 88.7 | 85.0 | | | | | |
| C3 | [mg][1] | 0 | 2 | 2 | 6 | 8 | 10 | 14 | \multicolumn{6}{l}{Experiment cancelled} |
| | [%][2] | 100 | 99.9 | 99.9 | 99.7 | 99.6 | 99.5 | 99.3 | | | | | |
| C4 | [mg][1] | 0 | 2 | 8 | 12 | 28 | 37 | 43 | \multicolumn{6}{l}{Experiment cancelled} |
| | [%][2] | 100 | 99.9 | 99.6 | 99.4 | 98.6 | 98.2 | 97.9 | | | | | |

[1] Weight loss in mg
[2] Weight in [%] based on the fill weight of 2000 mg

The data in Table 1 show that the polyethylene plastics conventionally used for pheromone release devices completely failed to ensure sufficient release of the pheromone of the six-dentated bark beetle, whereas plastic materials according to the invention ensure a release which matches the swarming period of the six-dentated bark beetle over a period of 3.5 months.

Study of the Performance for Trapping the Six-Dentated Bark Beetle in a Spruce Thicket:

The devices which have been filled with the pheromone were hung in slit traps from Theysohn on April 15, 2003. The location was a thicket of spruce (15 years old) in Bad Berka, Blankenhain District, 400 m above sea level. For each type of device, 3 traps were equipped. In this case, the number of six-dentated bark beetles caught in the 3 traps at a particular point in time and the total number of six-dentated bark beetles caught over the entire study period were determined. The data are shown in Table 3. On Jul. 29, 2003, all traps were reequipped, and the trapping performance was determined accordingly. The data are shown in Table 3.

TABLE 2

| | 24.4. | 29.4. | 6.5. | 13.5. | 20.5. | 27.5. | 3.6. | 10.6. |
|---|---|---|---|---|---|---|---|---|
| C5 | 77 | 336 | 1528 | 221 | 37 | 61 | 2893 | 6311 |
| 1 | 49 | 346 | 1391 | 417 | 34 | 672 | 3606 | 6270 |
| 2 | 43 | 239 | 2373 | 163 | 7 | 538 | 2539 | 5586 |

| | 17.6. | 24.6. | 1.7. | 8.7. | 15.7. | 22.7. | 29.7. | Total |
|---|---|---|---|---|---|---|---|---|
| C5 | 1488 | 188 | 198 | 51 | 54 | 56 | 24 | 13523 |
| 1 | 4123 | 2385 | 1778 | 421 | 1464 | 1384 | 3078 | 27519 |
| 2 | 4389 | 4450 | 715 | 163 | 1775 | 2612 | 2717 | 28309 |

TABLE 3

| | 6.8. | 12.8. | 19.8. | 2.9. | 9.9. | 16.9. | 25.9. | Total |
|---|---|---|---|---|---|---|---|---|
| C5 | 3233 | 2640 | 819 | 0 | 0 | 70 | 11 | 7792 |
| 1 | 3780 | 1896 | 967 | 6 | 0 | 90 | 21 | 8231 |
| 2 | 1810 | 2227 | 893 | 6 | 0 | 77 | 18 | 5597 |

The data in Table 2 show that the devices according to the invention are superior to a conventional dispenser in so far as they also ensure high trapping performance over a prolonged period of 3 months, whereas the conventional film-bag dispenser hardly shows any activity after approximately 2 months.

The data in Table 3 show that the devices according to the invention which are made of uncolored film material ensure a better trapping performance at the high temperatures in the measuring period than devices according to the invention from colored film material.

Study of the Performance for Trapping the Six-Dentated Bark Beetle in an Old Spruce Stand:

The devices which have been filled with the pheromone were hung in slit traps from Theysohn on Apr. 20, 2003. The location was an old spruce stand (80-90 years old) in Rübeland district, Harz, 400 m above sea level. For each type of device, 3 traps were equipped. The number of six-dentated bark beetles trapped in the 3 traps at a particular point in time and the total number of six-dentated bark beetles trapped over the entire duration of the study were determined in each case. The data are shown in Table 4.

TABLE 4

| Ex. | 30.4. | 9.5. | 16.5. | 25.5. | 3.6. | 10.6. |
|---|---|---|---|---|---|---|
| C5 | 5 | 616 | 2032 | 338 | 379 | 16335 |
| 1 | 90 | 818 | 1172 | 529 | 636 | 14610 |

| | 18.6. | 28.6. | 3.7. | 18.7. | 26.7. | Total |
|---|---|---|---|---|---|---|
| C5 | 11160 | 4639 | 2398 | 559 | 28 | 38489 |
| 1 | 8280 | 11339 | 1366 | 728 | 243 | 39811 |

A comparable study of the performance of trapping the six-dentated bark beetle which has been carried out over the period Apr. 28, 2002, through Jul. 6, 2002 in the Rübeland district, Harz, at 480 m above sea level in an old spruce stand (80-90 years old) showed that the trapping performance of the devices of Comparative Examples 1, 3 and 4 was less than 10% of the trapping performance of a conventional dispenser as described in Comparative Example 5.

What is claimed is:

1. A device in the form of a container made of a permeable plastic material which is exclusively an uncolored vinyl acetate/ethylene copolymer, which container comprises at least two sealed chambers, each of which comprises a liquid pheromone comprising 2-ethyl-1,6-dioxaspiro[4,4]nonane, methyl 2,4-decadienecarboxylate and at least one alcohol selected from the group consisting of 2-methylbut-3-en-2-ol and 2-methylbut-3-yn-2-ol, the liquid pheromone being completely enclosed within the interior of each chamber, where at least 70% of the area of the walls forming the chambers have a wall thickness in the range of from 0.1 to 1 mm and the plastic material which forms the chambers is an uncoated, uncolored vinyl acetate/ethylene copolymer with a vinyl acetate content in the range of from 10 to 17% by weight, where the ratio of the area of the walls forming the chambers to the internal volume of the chamber is in the range of from 1 to 10 cm$^{-1}$.

2. The device of claim 1, wherein the vinyl acetate/ethylene copolymer has a melt flow index in the range of from 1.8 to 3.2 g/10 min, as determined by the American Society for Testing and Materials' Standard Test Method for Melt Flow Rates of Thermoplastics by Extrusion Plastometer at 190° C. and 2.16 kg.

3. The device of claim 1, wherein the ratio of the area of the walls forming the chambers to the internal volume of the chamber is in the range of from 1 to 10 cm$^{-1}$.

4. The device of claim 1, wherein the chamber(s) has/have a tubular geometry with an internal diameter in the range of from 5 to 20 mm and a length in the range of from 20 to 40 mm.

5. The device of claim 1 with two separate chambers.

6. The device of claim 1, wherein the pheromone comprises
2 to 10% by weight of 2-ethyl-1,6-dioxaspiro[4,4]nonane;
0.5 to 5% by weight of methyl 2,4-decadienecarboxylate and
90 to 97.5% by weight of 2-methylbut-3-yn-2-ol and/or 2-methylbut-3-en-2-ol based on total weight of said pheromone.

7. The device of claim 1, comprising the pheromone in an amount of from 1 to 5 ml per chamber.

8. A method for combating the six-dentated bark beetle (*Pityogenes chalcographus*), which comprises providing one or more devices of claim 1 in conjunction with one or more trapping devices wherein said beetle is combated.

9. A method of monitoring the swarming of the six-dentated bark beetle comprising,
providing one or more devices of claim 1 in conjunction with one or more trapping devices and
checking said trapping device(s) for said beetle.

10. The method of claim 8, wherein said trapping devices are selected from the group consisting of trap wood piles, trap poles, trap brushwood piles and trap trees.

11. The method of claim 9, wherein said trapping devices are selected from the group consisting of trap wood piles, trap poles, trap brushwood piles and trap trees.

* * * * *